(12) United States Patent
Arnette et al.

(10) Patent No.: US 11,679,011 B2
(45) Date of Patent: Jun. 20, 2023

(54) PROSTHETIC COUPLING INTERFACES AND METHODS OF USE

(71) Applicant: ARNEX INNOVATIONS, LLC, Tulsa, OK (US)

(72) Inventors: Brandon Arnette, Claremore, OK (US); Jeffrey Arnette, Claremore, OK (US); Todd Hasenstein, Broken Arrow, OK (US)

(73) Assignee: Arnex Innovations, LLC, Tulsa, OK (US)

( * ) Notice: Subject to any disclaimer, the term of this patent is extended or adjusted under 35 U.S.C. 154(b) by 0 days.

(21) Appl. No.: 17/245,600

(22) Filed: Apr. 30, 2021

(65) Prior Publication Data

US 2022/0346983 A1 Nov. 3, 2022

(51) Int. Cl.
| | | |
|---|---|---|
| *A61F 2/78* | (2006.01) | |
| *A61F 2/60* | (2006.01) | |
| *A61B 17/62* | (2006.01) | |
| *A61F 2/66* | (2006.01) | |

(52) U.S. Cl.
CPC ............ *A61F 2/78* (2013.01); *A61F 2/60* (2013.01); *A61B 17/62* (2013.01); *A61F 2002/607* (2013.01); *A61F 2002/6614* (2013.01); *A61F 2002/7887* (2013.01)

(58) Field of Classification Search
CPC ........ A61F 2/78; A61F 2/60; A61F 2002/607; A61F 2002/7887; A61F 2/80; A61B 17/62
See application file for complete search history.

(56) References Cited

U.S. PATENT DOCUMENTS

2018/0303635 A1* 10/2018 Haun .................... A61F 2/80
2019/0046337 A1* 2/2019 Ramirez ................ A61F 2/76

OTHER PUBLICATIONS

Lam et al, Lengthening of Tibial after Trans-Tibial Amputation: Use of a Weight Bearing External Fixator-Prosthesis Composite, HDDJ 2016, 12:85-90, published online Sep. 8, 2015.*

* cited by examiner

*Primary Examiner* — Bruce E Snow
(74) *Attorney, Agent, or Firm* — Lexigent LLC

(57) ABSTRACT

Prosthetic coupling interfaces and methods of use are disclosed herein. An example system can include an external fixator apparatus, a prosthetic appendage assembly, and a prosthetic coupling interface for connecting the external fixator apparatus with the prosthetic appendage assembly.

4 Claims, 4 Drawing Sheets

PROSTHETIC COUPLING INTERFACES AND METHODS OF USE

CROSS REFERENCE TO RELATED APPLICATION(S)

N/A

FIELD OF TECHNOLOGY

The present disclosure is generally directed to prosthetic devices, and more particularly, but not by limitation, to prosthetic coupling interfaces and methods of use.

SUMMARY

According to some embodiments, the present disclosure is directed to a prosthetic coupling interface, comprising: a plate having a thickness and a lower surface, the plate comprising a plurality of equally spaced notches creating interface tabs, wherein a prosthetic appendage assembly is configured to couple with the lower surface of the plate, further wherein at least a portion of the interface tabs couple with mounting members of an external fixator apparatus.

In some instances, the each of the interface tabs comprises a centrally located coupling aperture. In one embodiment, an interface tab of the interface tabs is configured to be received within a receiver slot of a mounting member of the mounting members.

In some embodiments, the mounting member is aligned with the centrally located coupling aperture and a fastener extends through the mounting member to secure the mounting member to the interface tab. In various embodiments, the external fixator apparatus and the prosthetic appendage assembly are coupled together using the prosthetic coupling interface in such a way that a patient can walk using the prosthetic appendage assembly.

According to some embodiments, the present disclosure is directed to a system, comprising an external fixator apparatus; a prosthetic appendage assembly; and a prosthetic coupling interface for connecting the external fixator apparatus with the prosthetic appendage assembly.

In some embodiments, the prosthetic coupling interface comprises a plate having a thickness and a lower surface, the plate comprising a plurality of equally spaced notches creating interface tabs. In one embodiment, a prosthetic appendage assembly is configured to couple with the lower surface of the plate.

In additional embodiments, at least a portion of the interface tabs couple with mounting members of an external fixator apparatus. Each of the interface tabs comprises a centrally located coupling aperture. An interface tab of the interface tabs may be configured to be received within a receiver slot of a mounting member of the mounting members.

The mounting member can be aligned with the centrally located coupling aperture and a fastener extends through the mounting member to secure the mounting member to the interface tab the external fixator apparatus and the prosthetic appendage assembly are coupled together using the prosthetic coupling interface in such a way that a patient can walk using the prosthetic appendage assembly.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

The present disclosure pertains to prosthetic coupling interfaces that allow a patient to rapidly transition, post-operatively, to walking. For context, it is often psychologically difficult for a patient to wake up after an amputation surgery to visualize a missing appendage, such as a foot. While prosthetic devices exist for patients, these prosthetic devices are not configured to be placed onto the patient during their amputation surgery. This can be emotionally difficult for the patient. The prosthetic coupling interfaces of the present disclosure allow for placement of a prosthetic appendage, such a foot, onto a patient during surgery. The patient will awake with a prosthetic appendage, which may improve their self-confidence and overall mental well-being. Further, the patient can immediately begin walking on this prosthetic appendage improving patient outcomes.

Example Embodiments

Figure 1:
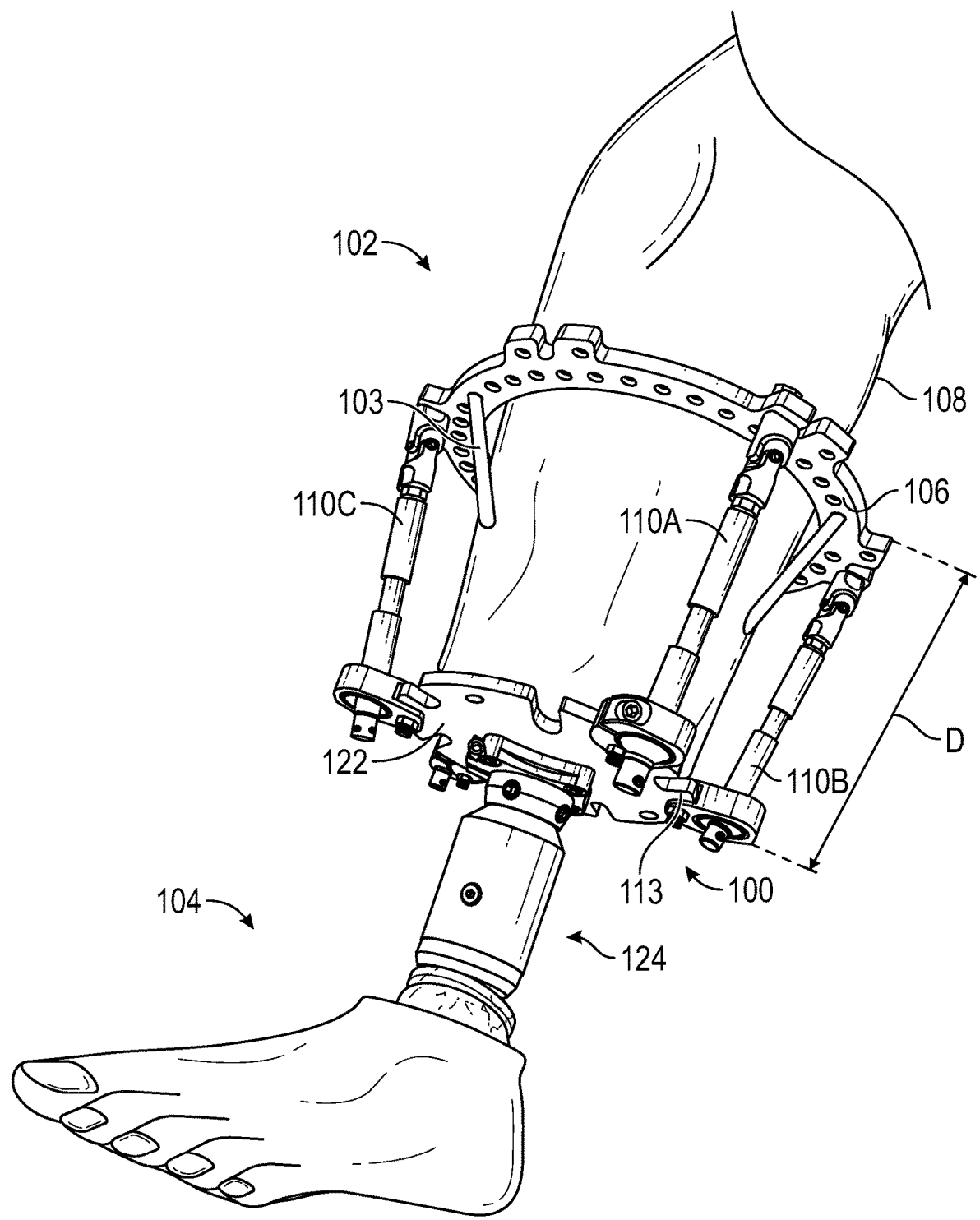
FIG. 1 is a perspective view of an example system comprising a prosthetic coupling interface for coupling an external fixation apparatus and a prosthetic appendage, the system being installed on a patient's leg.
Figure 2:
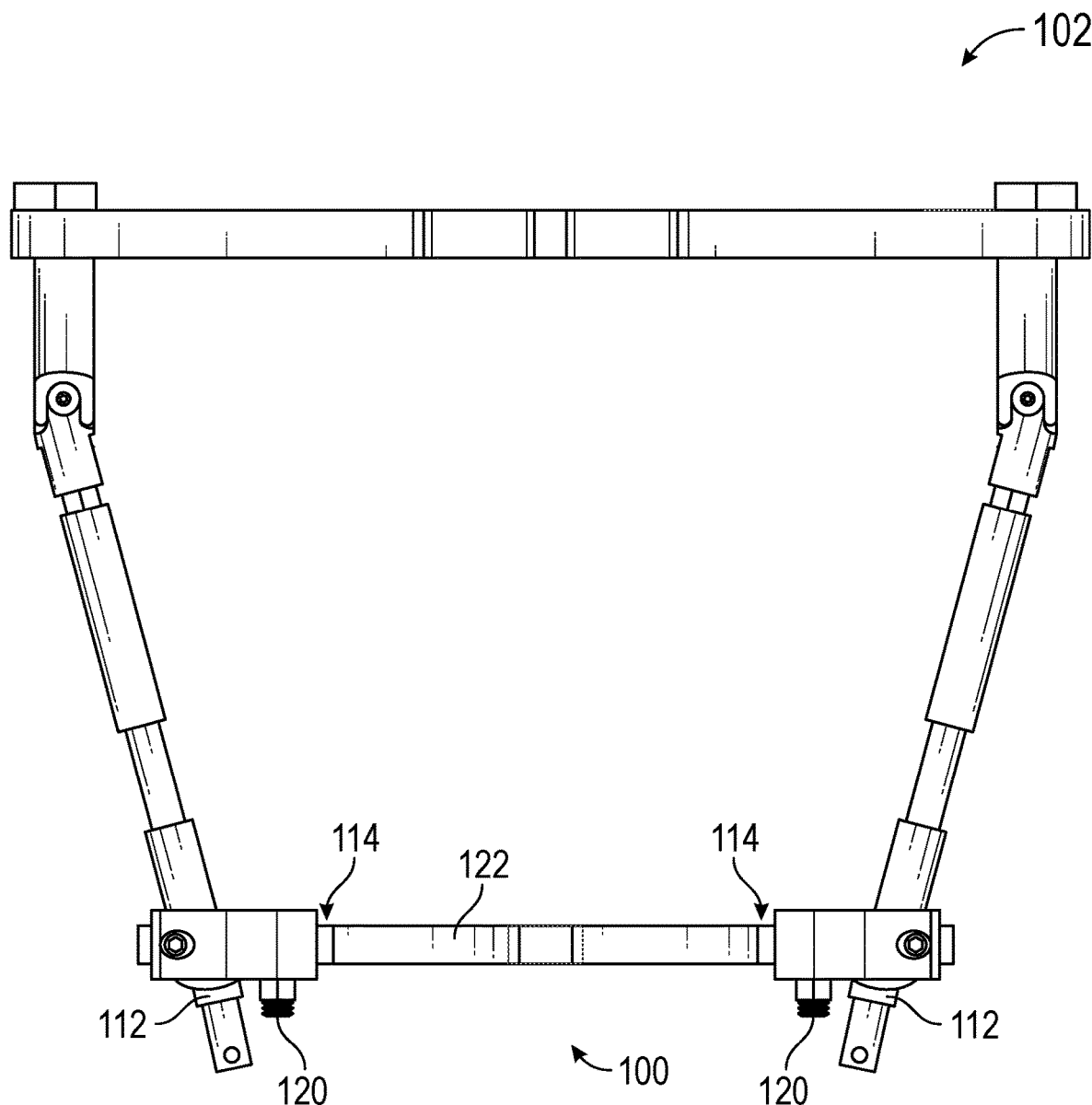
FIG. 2 is another perspective view of the example system.
Figure 3:
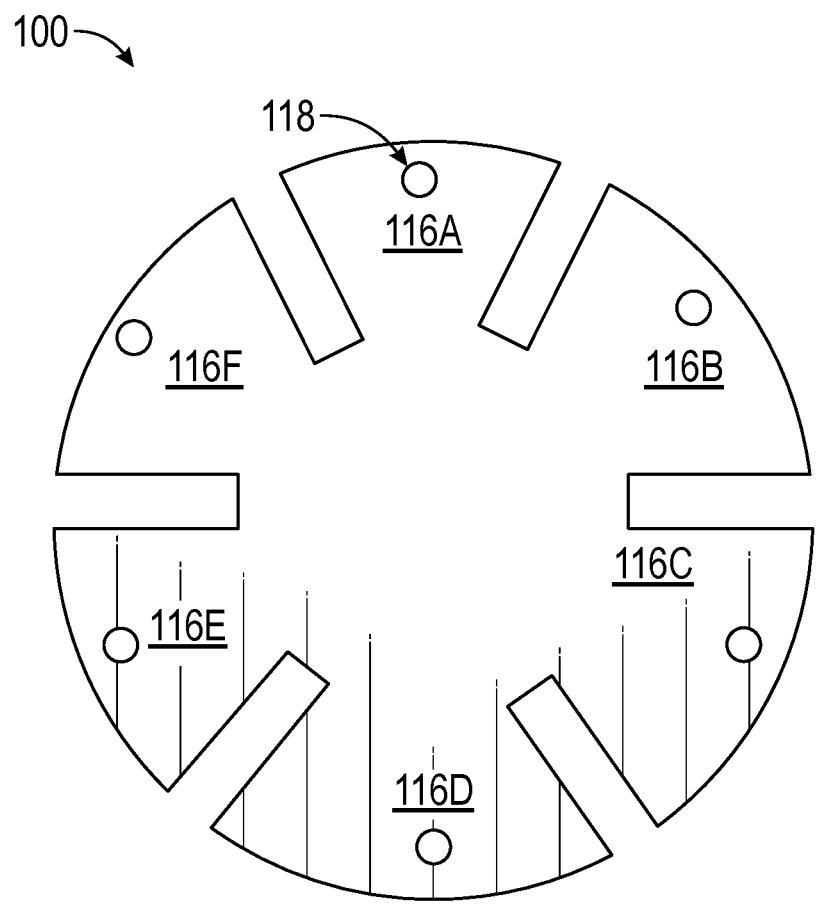
FIG. 3 is a top plan view of the example prosthetic coupling interface.
Figure 4:
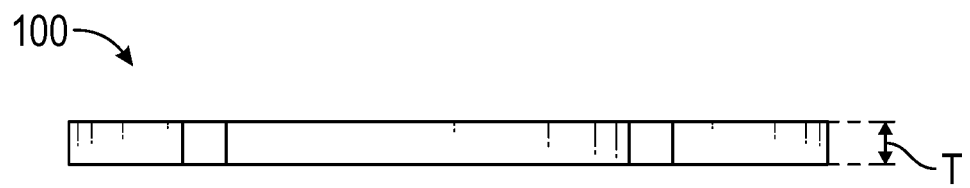
FIG. 4 is a side view of the example prosthetic coupling interface.

The following description will reference FIGS. 1-6 collectively. FIG. 1 is a perspective view of an example prosthetic coupling interface 100. Generally, the prosthetic coupling interface 100 provides a mechanical interface between an external fixator apparatus 102 and a prosthetic appendage 104. In this example, the prosthetic appendage 104 is a foot. The external fixator apparatus 102 can be fixed to the patient's leg with fixation guides, such as fixation guide 103. The fixation guides anchor the external fixator apparatus 102 to the leg bones such as the tibia and/or fibula.

In some embodiments, the external fixator apparatus 102 has a circular frame 106. The circular frame 106 encircles a lower leg 108 of a patient. The fixation guides can couple with and extend from the circular frame 106.

In general, the external fixator apparatus 102 may be utilized in other medical procedures, such as stabilizing a portion of a leg and/or foot of a patient. In some instances, the external fixator apparatus 102 can be used in trauma situations involving the leg, the ankle, and/or the foot. The external fixator apparatus 102 can be used in the treatment of foot and ankle deformities, fractures and fusions. These devices do not currently have applications related to treating a patient having a foot amputation.

The circular frame 106 can be coupled to the prosthetic coupling interface 100 using a plurality of struts, such as struts 110A, 110B, 110C, and 110D. For brevity and clarity, only one of the struts will be discussed in detail. The strut 110A is pivotally coupled to the circular frame 106 at one end. In some instances, the coupling is with a ball joint or other multi-axial joint. The strut 110A can telescope so that it's overall length can be adjusted. That is, the strut 110A can be lengthened or shortened as desired to vary a distance D between the prosthetic coupling interface 100 and the circular frame 106 of the external fixator apparatus 102. The strut 110A also comprises a mounting member 112 that can interface with the prosthetic coupling interface 100, as will be discussed in greater detail infra.

In one embodiment, the prosthetic coupling interface 100 is a circular plate. While a circularly shaped plate is disclosed, other shapes, including known geometrical shapes, as well as irregular shapes, can be utilized in accordance with the present disclosure.

In one embodiment, the prosthetic coupling interface 100 has a thickness T. The thickness T of the prosthetic coupling interface 100 can vary according to engineering and/or design requirements. In one example, the thickness T of the prosthetic coupling interface 100 can be based on an estimated weight of the patient. The prosthetic coupling interface 100 can be manufactured from any desired material including, but not limited to, a plastic or polymeric material, natural materials, man-made materials such as carbon fiber, composite materials, as well as other materials that would be known to one of ordinary skill in the art with the present disclosure before them.

The prosthetic coupling interface 100 comprises a plurality of notches, such as notch 114. Adjacent notches define interface tabs. In the illustrated embodiment, the prosthetic coupling interface 100 includes interface tabs 116A, 116B, 116C, 116D, 116E, and 116F. Fewer or additional interface tabs can be included, as would be appreciated by one or ordinary skill in the art. One or more of the interface tabs may comprise a centrally located coupling aperture. For example, interface tab 116A comprises a coupling aperture 118.

The mounting member 112 includes a receiver groove or slot 113 that receives an interface tab of the prosthetic coupling interface 100. For example, the receiver slot of the mounting member 112 of the strut 110A couples with the interface tab 116A. The mounting member 112 includes fastener apertures that align with the coupling aperture 118. A fastener 120 such as a threaded bolt and nut are used to secure the mounting member 112 to the interface tab 116A. While a threaded bolt and nut have been disclosed, other suitable connectors can be used.

The prosthetic appendage 104 can be attached to a lower or bottom surface 122 of the mounting member 112. In some embodiments, the mounting member 112 prosthetic appendage 104 is attached to a center point of the mounting member 112, so as to ensure proper weight distribution of the patient's leg over the prosthetic appendage 104. In some embodiments, the prosthetic appendage 104 is part of a prosthetic appendage assembly that includes a shaft 124. The shaft 124 includes a mounting plate 126 that may be connected to the mounting member 112 using fasteners such as screws.

Figure 5:
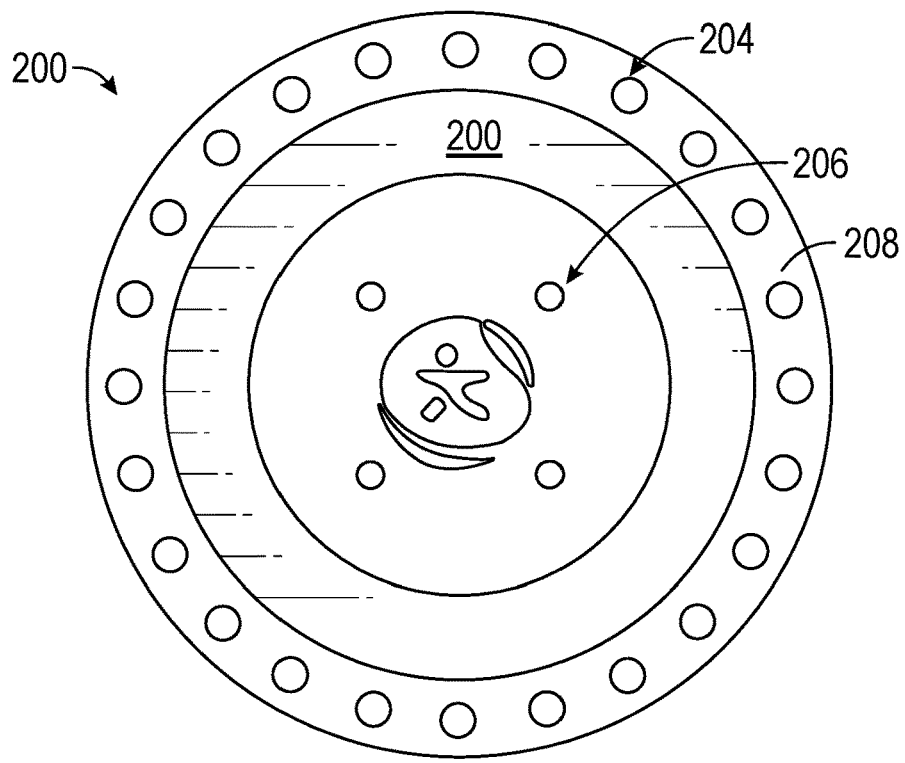
FIG. 5 is a plan view of another example prosthetic coupling interface.
Figure 6:
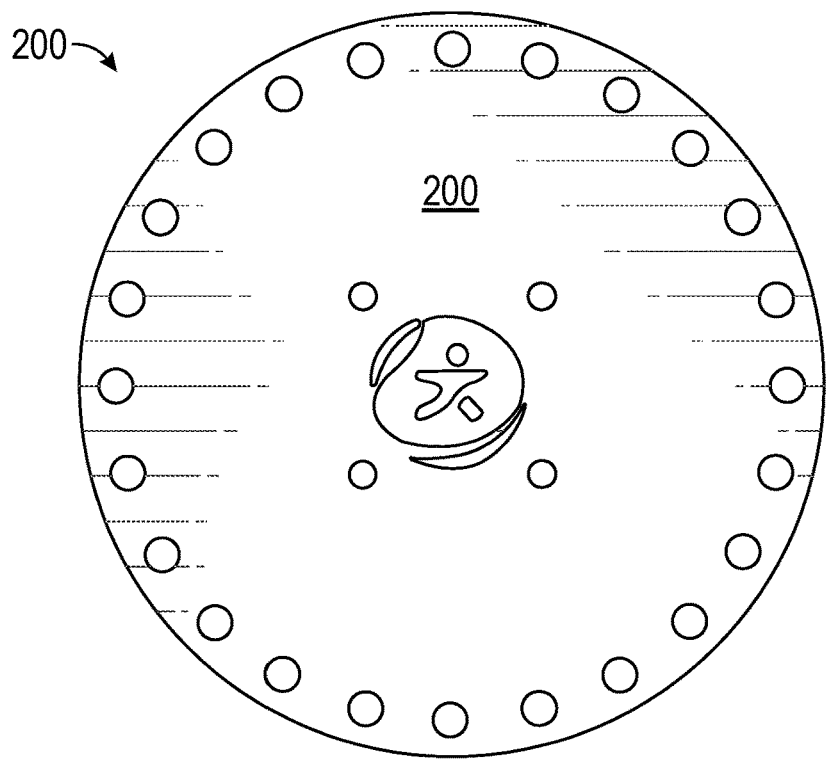
FIG. 6 is an opposite plan view of the example prosthetic coupling interface of FIG. 5.

FIGS. 5 and 6 collectively illustrate another example prosthetic coupling interface (device 200). The device 200 has a substantially uniform and circular body 202. The body 202 comprise an annular ring of apertures, such as aperture 204 that provide a coupling point for a mounting member (such as the mounting member 112 of FIGS. 1 and 2). The body 202 can have a consistent thickness. In some embodiments, the thickness of the body 202 can vary. For example, the thickness can be greater towards the outer peripheral edge 208 of the body 202. In another embodiment, the thickness can be greater towards the center of the body 202 and taper down towards the outer peripheral edge. The body 202 can also comprise a set of prosthetic appendage mounting apertures, such as aperture 206 that receive fasteners in order to couple a prosthetic appendage to the device 200. In some instances, the body 202 can comprise indicia, such as a logo that is centrally positioned.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three-dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A system, comprising:
   an external fixator apparatus;
   a prosthetic appendage assembly; and
   a prosthetic coupling interface for connecting the external fixator apparatus with the prosthetic appendage assembly, wherein the prosthetic coupling interface comprises a plate having a thickness and a lower surface, the plate comprising a plurality of equally spaced notches creating interface tabs, said prosthetic appendage assembly is configured to couple with the lower surface of the plate, wherein at least a portion of the interface tabs couple with mounting members of an external fixator apparatus and each of the interface tabs comprises a centrally located coupling aperture, wherein an interface tab of the interface tabs is configured to be received within a receiver slot of a mounting member of the mounting members.

2. The system according to claim 1, wherein the mounting member is aligned with the centrally located coupling aperture and a fastener extends through the mounting member to secure the mounting member to the interface tab.

3. The system according to claim 1, wherein the external fixator apparatus and the prosthetic appendage assembly are coupled together using the prosthetic coupling interface in such a way that a patient can walk using the prosthetic appendage assembly.

4. A system, comprising:
   an external fixator apparatus comprising:
      a circular frame configured to encircle a lower leg of a patient; and
      a plurality of struts positioned around the circular frame;
   a prosthetic coupling interface in the form of a plate, the prosthetic coupling interface comprising a plurality of interface tabs, wherein at least a portion of the interface tabs couple with mounting members of an external fixator apparatus and each of the interface tabs comprises a centrally located coupling aperture, wherein an interface tab of the interface tabs is configured to be received within a receiver slot of a mounting member of the mounting members; and
   a prosthetic appendage assembly attached to an underside of the prosthetic coupling interface, the external fixator apparatus and the prosthetic appendage assembly are coupled together using the prosthetic coupling interface in such a way that a patient can walk using the prosthetic appendage assembly.

\* \* \* \* \*